US 6,719,749 B1

(12) United States Patent
Schweikert et al.

(10) Patent No.: US 6,719,749 B1
(45) Date of Patent: Apr. 13, 2004

(54) MULTILUMEN CATHETER ASSEMBLY AND METHODS FOR MAKING AND INSERTING THE SAME

(75) Inventors: Timothy Schweikert, Levittown, PA (US); Anthony J. Madison, Lansdale, PA (US); Donald A. Schon, Paradise Valley, AZ (US)

(73) Assignee: Medical Components, Inc., Harleysville, PA (US)

( * ) Notice: Subject to any disclaimer, the term of this patent is extended or adjusted under 35 U.S.C. 154(b) by 335 days.

(21) Appl. No.: 09/585,149

(22) Filed: Jun. 1, 2000

(51) Int. Cl.⁷ ............................................. A61M 27/00
(52) U.S. Cl. ........................... 604/544; 604/43; 604/28
(58) Field of Search ............................. 604/544, 523, 604/534, 535, 284, 96.01, 536, 43

(56) References Cited

U.S. PATENT DOCUMENTS

| 701,075 | A | 5/1902 | McCully |
| 2,286,462 | A | 6/1942 | Chaffin |
| 3,144,868 | A | 8/1964 | Jascalevich |
| 3,359,974 | A | 12/1967 | Khalil |
| 3,400,714 | A | 9/1968 | Sheridan |
| 3,804,097 | A | 4/1974 | Rudie |
| 3,823,720 | A | 7/1974 | Tribble |
| 3,863,632 | A | 2/1975 | Schwartz |
| 4,072,146 | A | 2/1978 | Howes |
| 4,098,275 | A | 7/1978 | Consalvo |
| 4,134,402 | A | 1/1979 | Mahurkar |
| 4,203,436 | A | 5/1980 | Grimsrud |
| 4,385,631 | A | 5/1983 | Uthmann |
| 4,402,683 | A | 9/1983 | Kopman |
| 4,405,313 | A | 9/1983 | Sisley et al. |

(List continued on next page.)

FOREIGN PATENT DOCUMENTS

| BE | 0834211 | 2/1978 |
| CA | 1092927 | 1/1981 |
| CA | 1193508 | 9/1985 |
| EP | 0 386 408 | 9/1990 |
| FR | 1285953 | 12/1962 |

OTHER PUBLICATIONS

Brochure Entitled "Schon Cath" (One Dual Catheter) Permanent Access, 2 pages (Jul. 1996).

(List continued on next page.)

*Primary Examiner*—Sang Y. Paik
*Assistant Examiner*—Vinod D. Patel
(74) *Attorney, Agent, or Firm*—Joseph E. Maenner; Monte & McGraw, P.C.

(57) ABSTRACT

A multilumen catheter assembly and methods for making and inserting the same are provided. The catheter assembly includes a unitary catheter and at least two distal end tubes which extend distally from the unitary catheter. The at least two lumens in the unitary catheter are in fluid communication with passageways through the distal end tubes. The catheter assembly may be made by extruding a unitary catheter tube having internal longitudinally extending lumens, then splitting the tube on its distal end portion to form distal end tubes. The tubes are then ground and polished to form a smooth surface on the exterior of the tubes. The catheter assembly may also be made by forming an outer layer on at least two longitudinally extending catheters while leaving two distally extending portions of the tubes outside the outer layer to form the distal end tubes. The multilumen catheter assembly may be inserted in a patient for acute and chronic catheterization and subcutaneously tunneled and inserted using a single insertion procedure while leaving the distal end tubes within the vessel capable of free movement and sealing the insertion site into an area to be catheterized.

10 Claims, 7 Drawing Sheets

U.S. PATENT DOCUMENTS

| | | | |
|---|---|---|---|
| 4,427,012 A | | 1/1984 | Miller |
| D272,651 S | | 2/1984 | Mahurkar |
| 4,432,752 A | | 2/1984 | Marlon |
| 4,451,252 A | | 5/1984 | Martin |
| 4,493,696 A | | 1/1985 | Uldall |
| 4,548,597 A | | 10/1985 | Nelson |
| 4,568,329 A | | 2/1986 | Mahurkar |
| 4,583,968 A | | 4/1986 | Mahurkar |
| 4,619,643 A | | 10/1986 | Bai |
| 4,623,327 A | | 11/1986 | Mahurkar |
| 4,654,032 A | | 3/1987 | Morales-George |
| 4,682,978 A | | 7/1987 | Martin |
| 4,692,141 A | | 9/1987 | Mahurkar |
| 4,770,652 A | | 9/1988 | Mahurkar |
| 4,808,155 A | | 2/1989 | Mahurkar |
| 4,842,582 A | | 6/1989 | Mahurkar |
| 4,895,561 A | | 1/1990 | Mahurkar |
| 4,898,669 A | | 2/1990 | Tesio |
| 4,925,452 A | | 5/1990 | Melinyshyn et al. |
| 5,053,004 A | | 10/1991 | Markel et al. |
| 5,053,023 A | | 10/1991 | Martin |
| 5,059,170 A | | 10/1991 | Cameron |
| 5,084,013 A | | 1/1992 | Takase |
| 5,100,395 A | * | 3/1992 | Rosenberg .................. 604/284 |
| 5,106,368 A | | 4/1992 | Uldall et al. |
| 5,107,856 A | | 4/1992 | Kristiansen et al. |
| 5,156,592 A | | 10/1992 | Martin et al. |
| 5,167,220 A | | 12/1992 | Brown |
| 5,171,216 A | | 12/1992 | Dasse et al. |
| 5,197,951 A | | 3/1993 | Mahurkar |
| 5,209,723 A | | 5/1993 | Twardowski et al. |
| 5,221,255 A | | 6/1993 | Mahurkar et al. |
| 5,221,256 A | | 6/1993 | Mahurkar |
| 5,236,016 A | | 8/1993 | Vogelsang |
| 5,318,517 A | | 6/1994 | Reiman |
| 5,334,167 A | | 8/1994 | Cocanower |
| 5,336,220 A | | 8/1994 | Ryan et al. |
| 5,338,308 A | | 8/1994 | Wilk |
| 5,346,471 A | | 9/1994 | Raulerson |
| 5,350,358 A | | 9/1994 | Martin |
| 5,374,245 A | | 12/1994 | Mahurkar |
| 5,378,230 A | | 1/1995 | Mahurkar |
| 5,378,241 A | | 1/1995 | Haindl |
| 5,380,276 A | * | 1/1995 | Miller et al. .................. 604/28 |
| 5,385,548 A | | 1/1995 | Williams et al. |
| 5,405,341 A | | 4/1995 | Martin |
| 5,480,380 A | | 1/1996 | Martin |
| 5,549,579 A | * | 8/1996 | Batdorf et al. .............. 604/264 |
| 5,562,618 A | | 10/1996 | Cai et al. |
| 5,599,304 A | * | 2/1997 | Shaari ..................... 604/94.01 |
| 5,624,413 A | | 4/1997 | Markel et al. |
| 5,683,640 A | * | 11/1997 | Miller et al. ................. 264/255 |
| 5,718,692 A | | 2/1998 | Schon et al. |
| 5,776,111 A | | 7/1998 | Tesio |
| 5,785,686 A | | 7/1998 | Runge |
| 5,800,414 A | | 9/1998 | Cazal |
| 5,807,311 A | | 9/1998 | Palestrant |
| 5,947,953 A | | 9/1999 | Ash et al. |
| 6,001,079 A | * | 12/1999 | Pourchez ..................... 604/43 |
| 6,074,374 A | * | 6/2000 | Fulton ......................... 604/249 |
| 6,190,349 B1 | * | 2/2001 | Ash et al. ..................... 604/43 |

OTHER PUBLICATIONS

Hocken, A.G., "Percutaneous Femoral Vein Catheterization for Hemodialysis: A Single Needle Technique,"*Clinical Nephrology,*vol. 12, No. 2, 1979, pp. 93–94.

Brochure entitled, "The MedComp TESIO Catheter", MEDCOMP, Harleysville, PA, date unknown, 4 pages.

B. Canaud, J.J. Beraud, H. Joyeux, C. Mion. "Internal Jugular Vein Cannulation with Two Silicone Rubber Catheters" *Artifical Organs,*1986; 10(5):397–403.

F. Tesio, et al. "Double Catheterization of the Internal Jugular Vein for Hemodialysis: Indications, Techniques and Results" *Artificial Organs*, 1994; 18(4):301–304.

Sheet listing three references, dated 1999 (Cook Critical Care).

* cited by examiner

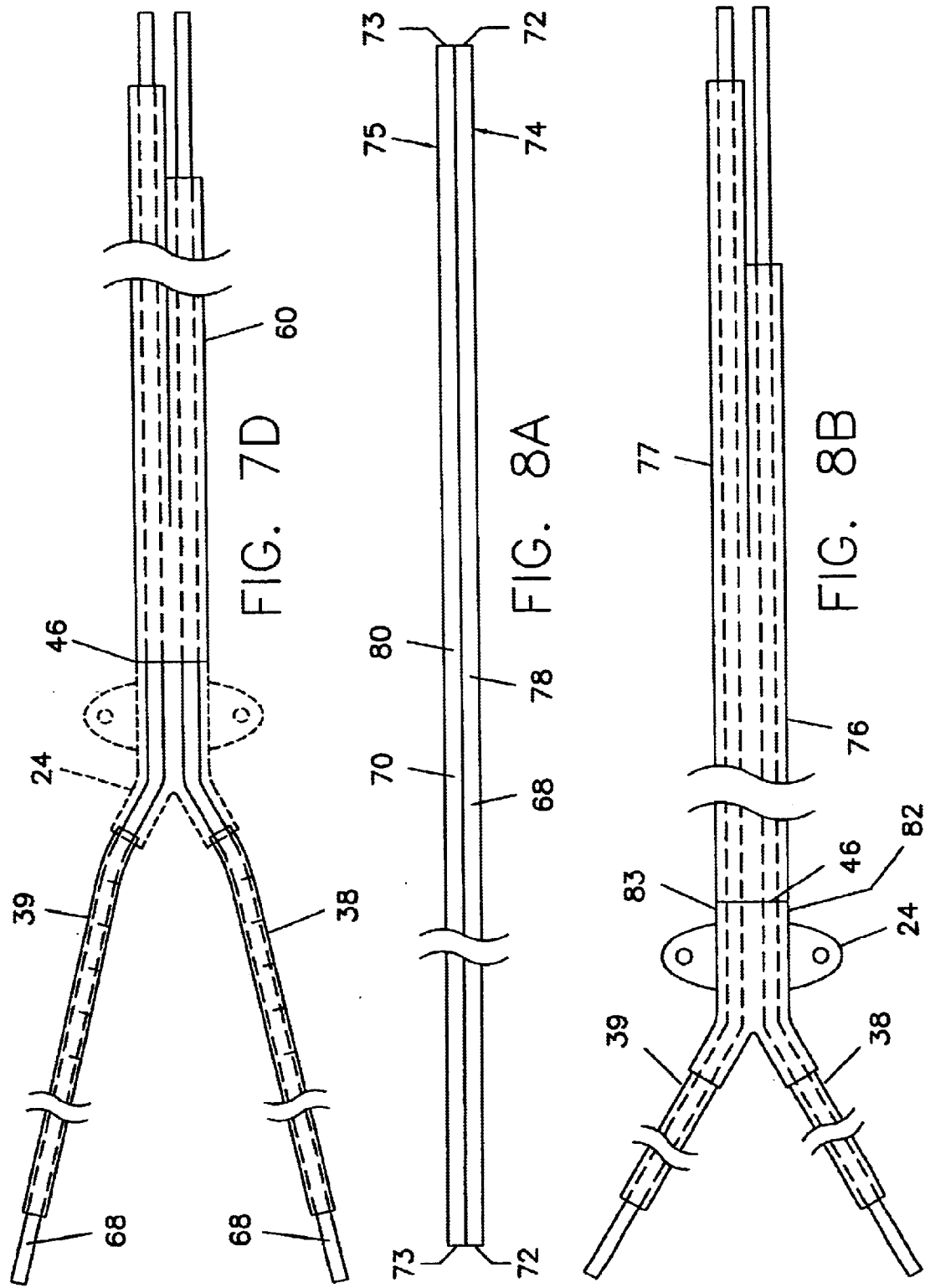

MULTILUMEN CATHETER ASSEMBLY AND METHODS FOR MAKING AND INSERTING THE SAME

BACKGROUND OF THE INVENTION

Catheters for the introduction or removal of fluids may be located in various venous locations and cavities throughout the body for the introduction or removal of fluids. Such catheterization may be performed by using a single catheter having multiple lumens. A typical example of a multiple lumen catheter is a dual lumen catheter in which one lumen introduces fluids and one lumen removes fluids. Catheterization may also be performed by using separate, single lumen catheters inserted through two different incisions into an area to be catheterized. Such multiple catheter assemblies are known as Tesio catheters. Procedures are also known as described in U.S. Pat. No. 5,624,413 for inserting two wholly independent single lumen catheters into a vessel through a single insertion site.

Generally, to insert any catheter in a blood vessel, the vessel is identified by aspiration with a long hollow needle in accordance with the Seldinger technique. When blood enters a syringe attached to the needle, indicating that the vessel has been found, a thin guide wire is then introduced, typically through a syringe needle or other introducer device, into the interior of the vessel. The introducer device is then removed leaving the guide wire within the vessel. The guide wire projects beyond the surface of the skin.

At this point, several options are available to a physician for catheter placement. The simplest is to pass a catheter into the vessel directly over the guide wire. The guide wire is then removed leaving the catheter in position within the vessel. However, this technique is only possible in cases where the catheter is of a relatively small diameter, made of a stiff material and not significantly larger than the guide wire, for example, for insertion of small diameter dual lumen catheters. If the catheter to be inserted is significantly larger than the guide wire, a dilator device is first passed over the guide wire to enlarge the hole. The catheter is then passed over the guide wire, and the guide wire and dilator are removed.

In the case of an individual, single-lumen catheter typically used in multiple catheter assemblies (e.g., a Tesio catheter), a physician may use an introducer sheath. If a Tesio is used for hemodialysis, for example, each catheter is inserted in two separate veins, such as the femoral vein. Alternatively, each catheter may be inserted in two different locations of the same vein, such as the internal jugular vein as noted above. The introducer sheath is simply a large, stiff thin-walled tube, which serves as a temporary conduit for the permanent catheter which is being placed. Tearaway sheaths are also available which split apart for easier removal. The introducer sheath is positioned by placing a dilator device inside of the introducer and passing both the dilator and the introducer together into the vessel over a guide wire. The guide wire, left in the vessel after insertion as described above, and the dilator are then removed, leaving the thin-walled introducer sheath in place. The catheter is placed through the introducer sheath. Each of the catheters in the assembly is typically subcutaneously secured within the patient's body by a cuff located in a subcutaneous tunnel, or by otherwise externally affixing the catheter to the body.

The Tesio catheter may also be inserted, in accordance with the technique described in U.S. Pat. No. 5,624,413 as noted above, through a single insertion point using a sheath into the vessel. The Tesio, once inserted in the vessel, is then tunneled separately through the patient in two subcutaneous tunnels for securement of the external, proximal portions of the catheter.

The Tesio double catheter assembly, while comfortable for the patient, due to its soft durometer, and very effective for hemodialysis, typically requires multiple procedures and incisions for insertion and/or for tunneling, which increase the attendant risks of the catheterization procedure. Further, in the case of side-by-side placement of two catheter tubes through a single insertion site in a vessel, while minimizing the number of procedures, can present a potential for leakage between the catheter tubes at the point where the catheter tubes pass into the vessel.

However, Tesio catheter assemblies provide catheters which are capable of independent movement within the vessel. Such catheters present several advantages over unitary multi-lumen catheters formed of a single internally divided tube when in the vessel. Because the individual tubes of a Tesio double catheter assembly are independently movable at their fluid outlets, it is possible to provide fluid intake and/or return flow around the entire circumference of the distal ends of the catheter tubes. In addition, if one tube becomes blocked, or otherwise requires replacement, it can be removed independently of the other tube. Further, the softer durometer of such catheters, which are typically made of a silicone or a similar material, reduces the risk of vessel wall damage. The 360° circumferential flow provides a more stable tube within the vessel, which is less likely to be suctioned against the vessel wall due to a pressure differential, as occasionally occurs in the use of some side-by-side multi-lumen catheters.

U.S. Pat. No. 5,718,692, issued to Schon, et al., ("the Schon catheter") describes a self-retaining double catheter system in which each catheter can be subcutaneously secured without the use of fabric tissue ingrowth cuffs or external suturing as a result of the placement of a retaining sleeve surrounding both individual catheters in a multiple catheter assembly to hold the catheters together at the location of the sleeve. The individual catheters are permanently linked in one portion by a hub for self-anchoring under the skin, as an alternative to requiring a fabric stabilizing cuff, such that such cuffs are optional. The distal ends are longitudinally prespaced by an appropriate distance to avoid recirculation. While this device requires only one incision, it requires two subcutaneous tunnels in order to facilitate the self-retaining feature. This catheter provides independently movable distal ends within the vessel and 360° circumferential flow in the manner of a standard Tesio. Further, since the retaining sleeve is located outside the vessel when in place to provide the self-retaining feature, at the point of entry into the vessel, the catheters are side-by-side in the manner of a standard Tesio catheter, and there still remains the potential risk of blood leakage between the catheters at the vessel site.

U.S. Pat. No. 5,947,953 discloses a splittable multiple catheter assembly that has a hub and at least two fully independent catheter tubes which are initially releasably joined together, for example, by a breakable membrane. A single subcutaneous tunnel may be used in inserting the catheter, and the catheter tubes are at least partially separated by splitting the catheter tubes prior to insertion into a vessel. As a result, the portions of the catheter within the vessel are capable of independently moving and having 360° circumferential flow from the distal portion of each tube. The catheter may be secured using standard securement means such as suturing, ingrowth or other available securement devices.

A further multiple catheter assembly is described in U.S. Pat. No. 5,776,111 for use in acute Tesio catheterizations. The assembly includes two independent single lumen catheters joined at a location by a generally flat disc that may be attached to the surface of a patient's skin to secure the assembly in an acute procedure. The distal ends are prespaced to avoid recirculation.

There is a need in the art for a multiple catheter assembly and a need for making such a catheter assembly which can provide the advantages of the above-mentioned multi-lumen catheters with respect to easy insertion through a single tunneling procedure and which prevents the potential risk of leakage at the site of vessel entry, but which can still provide the advantage of multiple catheter assemblies with respect to independent movement within a vessel and good flow properties.

SUMMARY OF THE INVENTION

The present invention provides a method of making a multilumen catheter assembly, comprising forming a unitary catheter tube to have a distal portion and a distal end portion terminating in a distal end, a proximal portion terminating in a proximal end, and a first lumen and a second lumen, each of the first lumen and the second lumen extending longitudinally through the unitary catheter tube; and splitting the unitary catheter tube longitudinally along the distal end portion of the unitary catheter tube to form a first distal end tube and a second distal end tube.

The invention further includes a method of making a multilumen catheter assembly, comprising arranging a first catheter having a distal end, a distal end portion and at least one first lumen extending longitudinally therethrough and a second catheter having a distal end, a distal end portion and at least one second lumen extending longitudinally therethrough such that the first catheter and the second catheter are substantially longitudinally parallel; and forming an outer layer around at least a portion of an exterior surface of the first catheter proximal to the distal end portion of the first catheter and around at least a portion of an exterior surface of the second catheter proximal to the distal end portion of the second catheter such that first catheter and the second catheter are fixed within the outer layer, the first lumen and the second lumen are generally parallel within the outer layer and the distal end portions of the first and second catheters extend outwardly and distally from the portions of the exterior surfaces of the first and second catheters which are within the outer layer and the distal end portions are capable of independent movement.

The invention also includes, in one embodiment, a method of making a multilumen catheter assembly which comprises forming a unitary catheter tube to have a distal portion and a distal end portion terminating in a distal end, a proximal portion terminating in a proximal end, and a first lumen and a second lumen, each of the first lumen and the second lumen extending longitudinally through the unitary catheter tube; forming a first distal end tube having a first passageway extending longitudinally therethrough and a second distal end tube having a second passageway extending longitudinally therethrough; and attaching the first and second distal end tubes to the distal end of the unitary catheter tube such that the first passageway in the first distal end tube is in communication with the first lumen of the unitary catheter tube and the second passageway in the second distal end tube is in communication with the second lumen in the unitary catheter tube.

A multilumen catheter assembly is included in the invention which comprises a unitary catheter having an exterior surface and a first lumen and a second lumen extending longitudinally therethrough, a distal end and a proximal end; and a first distal end tube defining a first longitudinally extending passageway and a second distal end tube defining a second longitudinally extending passageway, wherein the first and second distal end tubes extend distally from the distal end of the unitary catheter, the first passageway in the first distal end tube is in fluid communication with the first lumen, the second passageway in the second distal end tube is in fluid communication with the second lumen and the first and second distal end tubes are capable of independent movement with respect to each other.

The invention also encompasses a method for inserting a multilumen catheter assembly into an area of a body to be catheterized. The multilumen catheter assembly comprises a unitary catheter having an exterior surface and at least a first lumen and a second lumen extending longitudinally therethrough, a distal end and a proximal end; and at least a first distal end tube defining a first longitudinally extending passageway and a second distal end tube defining a second longitudinally extending passageway, wherein the first and second distal end tubes extend distally from the distal end of the unitary catheter, the first passageway in the first distal end tube is in fluid communication with the first lumen, the second passageway in the second distal end tube is in fluid communication with the second lumen and the first and second distal end tubes are capable of independent movement with respect to each other. The method comprises making an incision near the area to be catheterized; inserting the first and second distal end tubes through the incision and into the area to be catheterized until the first and second distal end tubes are fully within the area to be catheterized and a portion of the unitary catheter extends into the area to be catheterized; and securing the proximal end of the unitary catheter.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings, the same reference numerals are employed for designating the same elements throughout the several figures. In the drawings:

FIG. 7D is a partially broken away plan view of the unitary catheter tube of FIG. 7C on metal rods which are also inserted into first and second extension tubes prior to molding a hub in accordance with the invention;

FIG. 8A is a partially broken away plan view of a first and second catheter for use in making a multilumen catheter assembly according to a further embodiment of the invention;

FIG. 8B is a partially broken away plan view of the first and second catheters of FIG. 8A having an outer layer formed over a portion of the catheters, metal rods inserted within the catheters for placing the catheters in rigid position while molding a hub around the catheters at the proximal end of the outer layer.

DETAILED DESCRIPTION OF THE INVENTION

Figure 1:
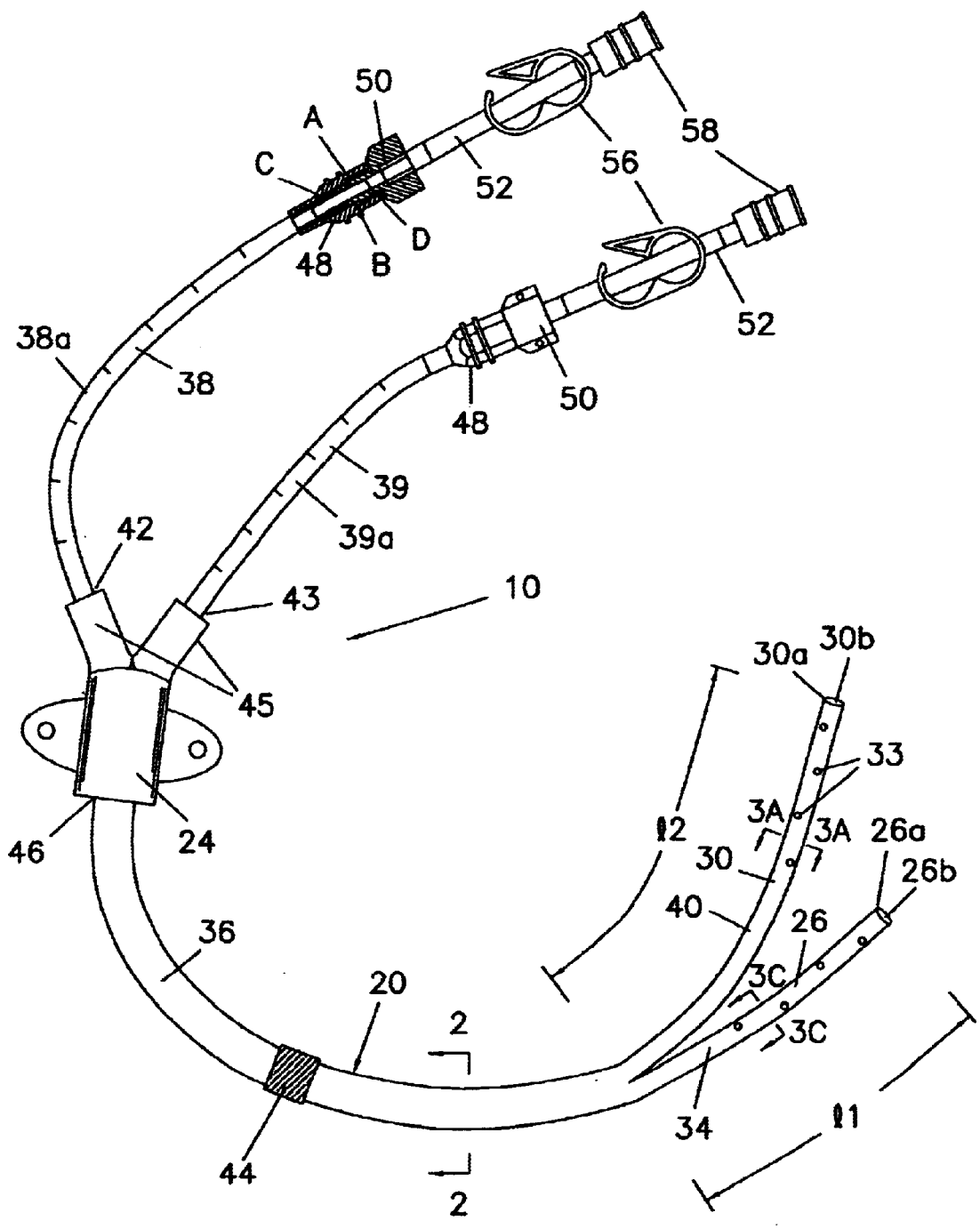
FIG. 1 is a perspective view of a multilumen catheter assembly in accordance with an embodiment of the present invention.

Certain terminology is used herein for convenience only and is not to be taken as a limitation on the present invention. The words "right," "left," "outwardly" and "inwardly" designate directions in the drawings to which reference is made. The words "proximal" and "distal" refer to directions away from and closer to, respectively, the insertion tips of the first and second catheters in the multiple catheter assembly according to the present invention. The terminology includes the words above specifically mentioned, derivatives thereof, and words of similar import.

The following describes preferred embodiments of the invention. However, it should be understood, based on this disclosure, that the invention is not limited by the preferred embodiments described herein. Referring now to the drawings in detail, there are shown in FIG. 1, a preferred embodiment of a multilumen catheter assembly generally indicated as 10, according to the invention. The multilumen catheter assembly 10 shown in FIG. 1 is a double catheter assembly, although assemblies having three or more lumens and distal end tubes are within the scope of the invention. Further, the methods for making such catheters are described in detail below are also applicable to making assemblies having more than two lumens and distal end tubes. The present description, however, for convenience purposes describes the assembly based on a two lumen embodiment.

Figure 4:
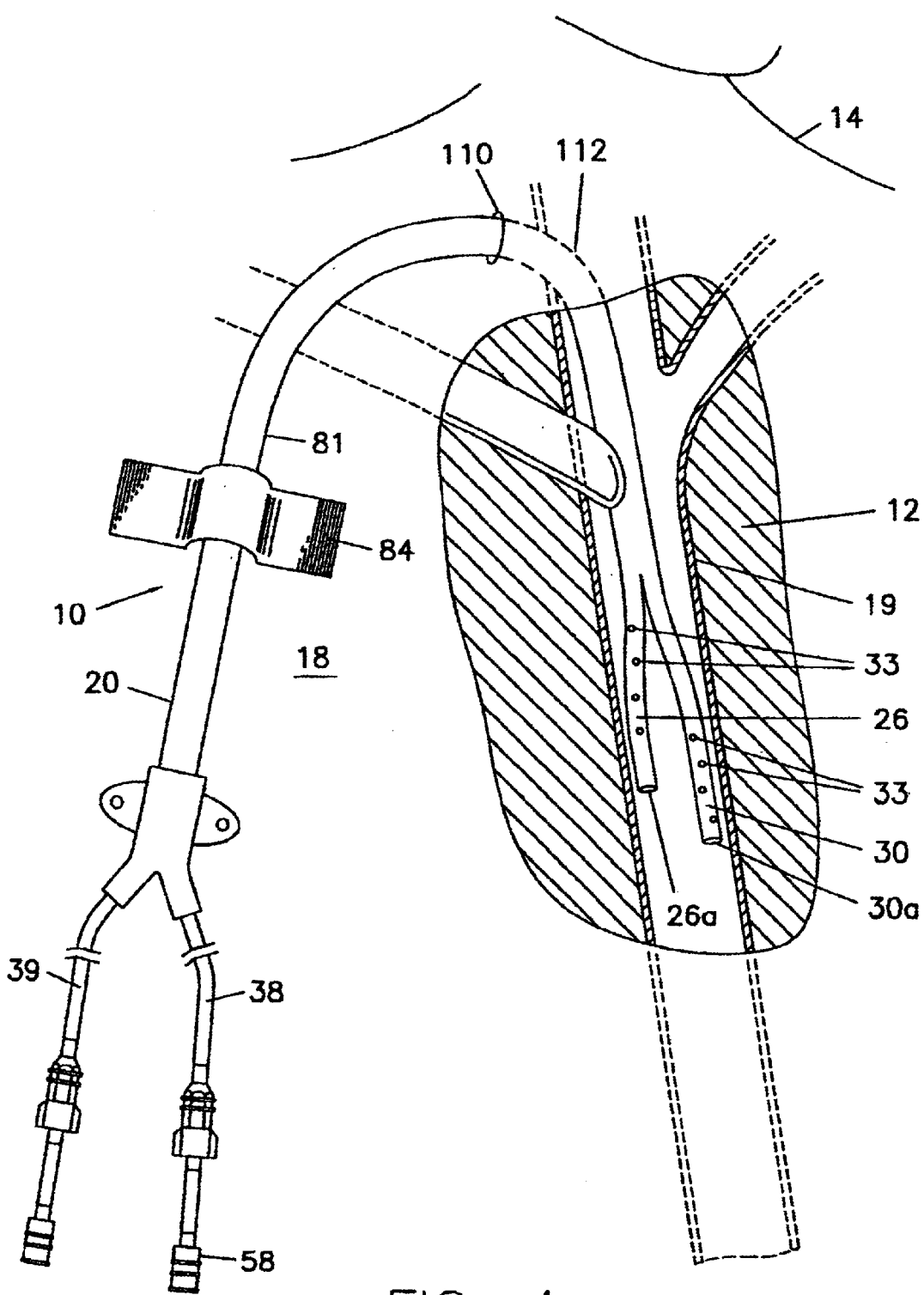
FIG. 4 is a partially broken-away diagrammatic view of a multilumen catheter assembly which has been inserted into an area to be catheterized, in accordance with a method of inserting a multilumen catheter assembly according to the present invention.
Figure 5:
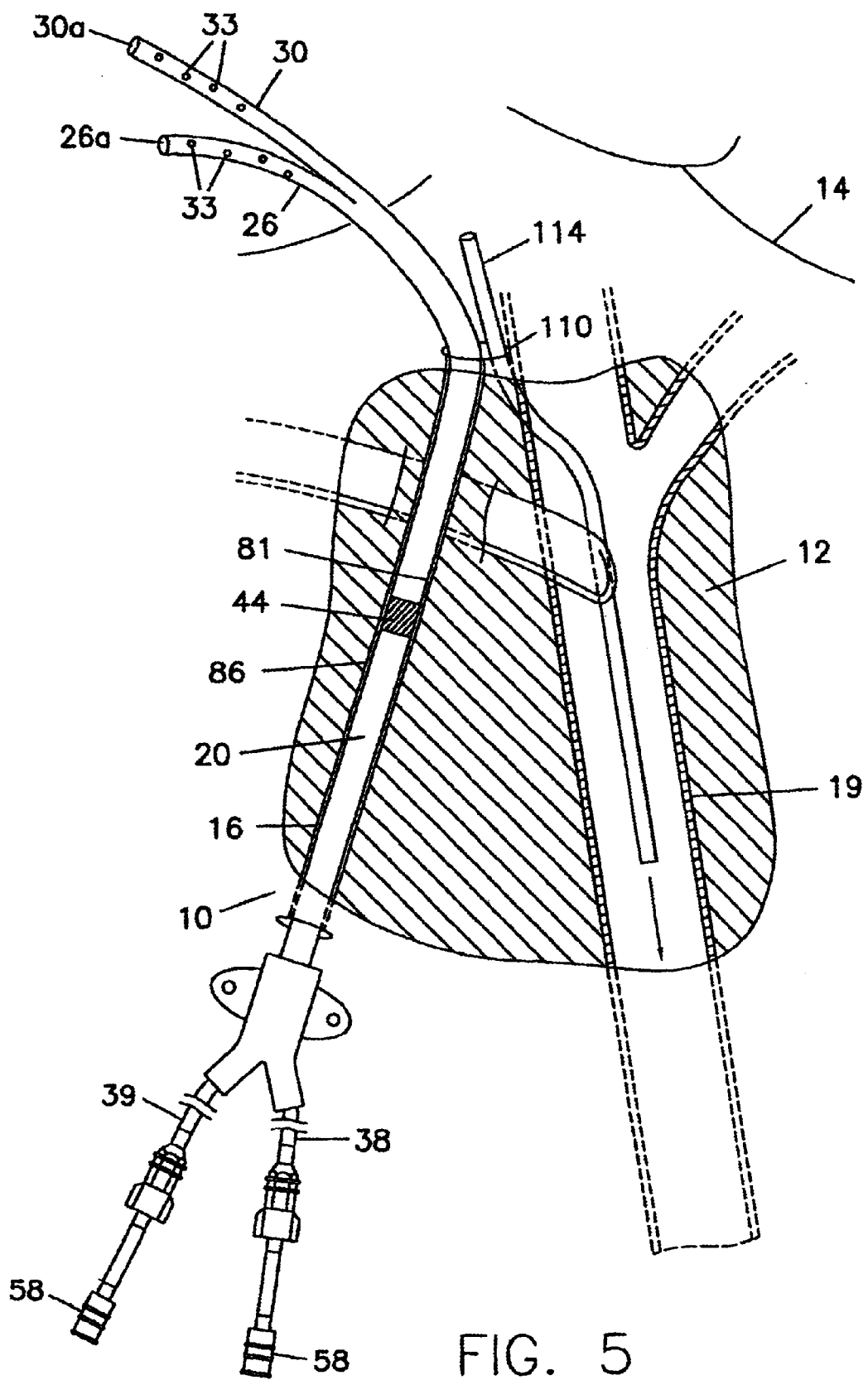
FIG. 5 is a partially broken-away diagrammatic view of a multilumen catheter assembly subcutaneously tunneled in a body before insertion into an area to be catheterized, in accordance with one embodiment of a method for inserting a multiple catheter assembly in accordance with the invention.
Figure 6:
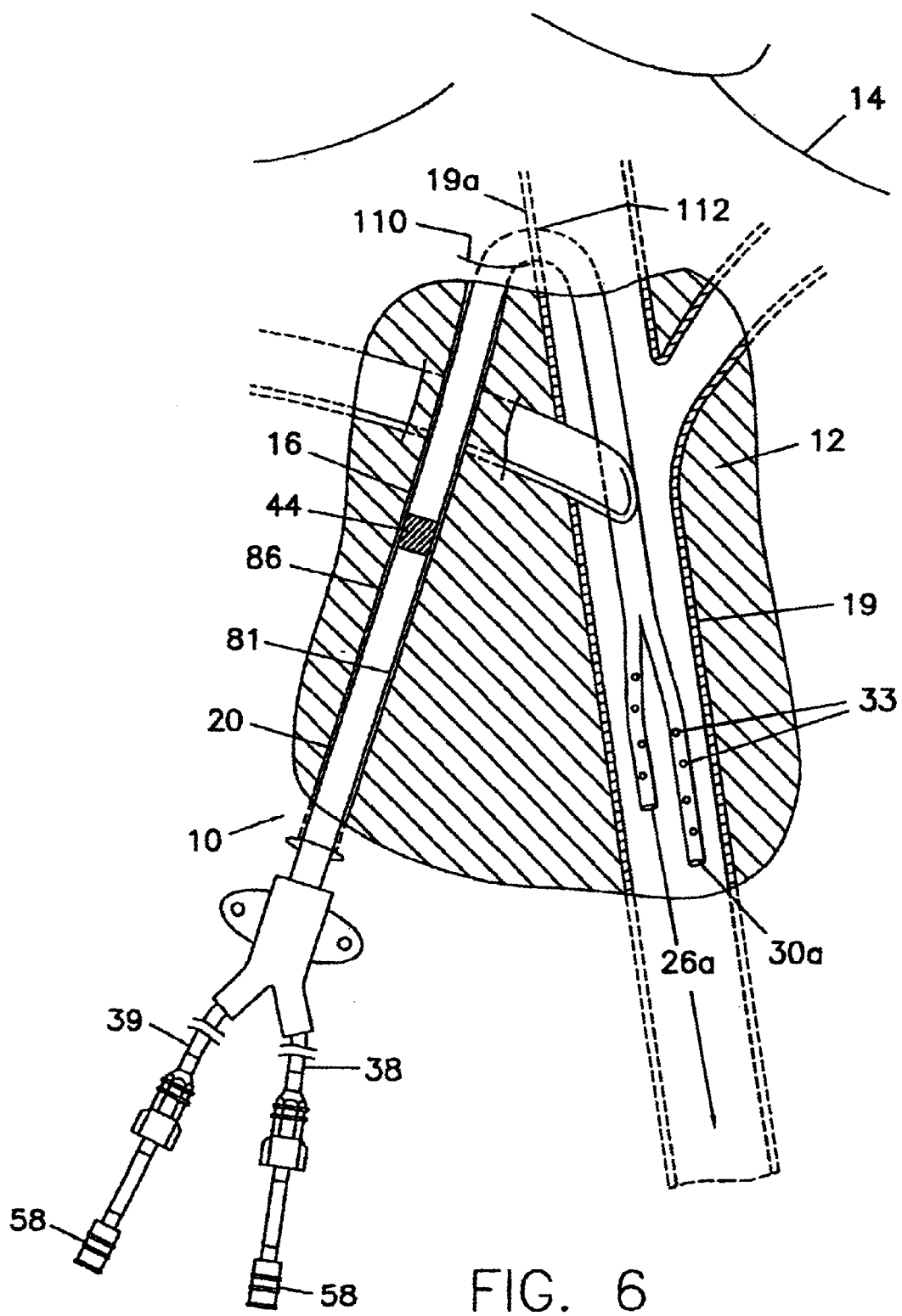
FIG. 6 is a partially broken-away diagrammatic view of a multiple catheter assembly of FIG. 5 in which the distal end tubes of the assembly are inserted into the area to be catheterized.

Referring to FIGS. 4–6, and as described in further detail below, a multilumen catheter assembly according to the present invention is inserted into a patient and into an area 12 of a body 14 to be catheterized for removing and introducing fluids to the area 12. The catheter assembly 10 is secured to a fixed location in or on the body 14, such as a subcutaneous area 16, as shown in FIGS. 5 and 6, in the body 14 before it is properly inserted and positioned in the catheterization area 12. This method is particularly preferred for chronic catheterization. Alternatively, in an acute catheterization, the catheter assembly 10 may be secured to an external surface 18 of the body 14, as shown in FIG. 4, before or after it is properly inserted and positioned in the catheterization area 12.

The multilumen catheter assembly 10 of the present invention can be adapted for use in various applications in which bodily fluids, medicaments or other solutions are introduced into and removed from the body such as perfusion, infusion, plasmapheresis, hemodialysis, chemotherapy, and the like. The catheter assembly 10 is particularly suitable for chronic hemodialysis and apheresis. The area to be catheterized is preferably a blood vessel such as an internal jugular vein, but may be any suitable area within the body. Other areas in which the catheter assembly may be used include, for example, other blood vessels, including the femoral and subclavian veins, any abscess cavity, post-operative cavity, the peritoneal cavity, and other areas of the body including intra-abdominal, sub-diaphragmatic and sub-hepatic areas. It should be understood by one of ordinary skill in the art from this disclosure that these areas are exemplary, and that the catheter assembly may be used to remove or introduce fluids in various areas to be catheterized.

The embodiment of the invention shown in FIG. 1 is particularly useful for intake, or removal, of blood to be purified from a blood vessel, such as the internal jugular vein, and introduction of purified blood into the same vessel. The blood can be purified by any suitable hemodialysis apparatus (not shown) attached in communication with the lumens of the catheter assembly of the invention 10. The catheter assembly 10 may also be used to introduce medication or other fluids including glucose or saline solutions into the body.

For the purposes of describing the preferred embodiment of the present invention, the device will be described with respect to the preferred application of hemodialysis, more specifically, for purifying blood flowing through the internal jugular vein 19. However, it will be understood by one skilled in the art based on this disclosure, that the assembly can be configured and adapted, by increasing or decreasing the size (diameter or length) and/or number of distal end tubes and/or lumens in the assembly, such that the assembly can be beneficially used for other medical applications in which fluids are introduced into and/or removed from the body.

Figure 2:
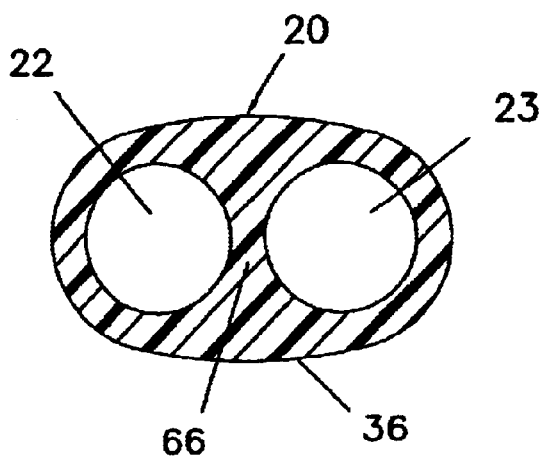
FIG. 2 is an enlarged cross-sectional view of the multilumen catheter assembly of FIG. 1, taken along line 2—2.

Referring now to the embodiment of FIG. 1 and FIGS. 3A and 3C, the multilumen catheter assembly 10 includes a unitary catheter 20, and an optional hub 24, as described in more detail below. The assembly 10 further includes a first distal end tube 26 which has an outer surface 34 defining a first passageway 28 extending longitudinally through the distal end tube 26. A second distal end tube 30 has an outer surface 40 defining a second longitudinally extending passageway 32. The first and second passageways 28, 32 are in fluid communication with, respectively, a first lumen 22 and second lumen 23 which extend through the full length of the unitary catheter 20 as shown in FIG. 1 and 2. The distal end tubes 26,30 are preferably have outer surfaces which are continuous with the outer surface of the unitary catheter on the outer portion and extend distally from the distal end 31 of the unitary catheter. The distal end tubes 36, 30 are capable of independent movement and are not attached to each other, but only to the unitary catheter 20.

Figure 3A:
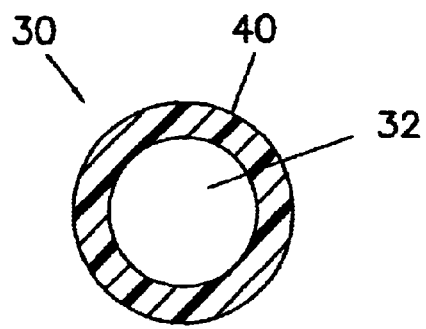
FIG. 3A is a cross sectional view of a distal end tube of the multilumen catheter assembly of FIG. 1 taken along line 3A—3A.
Figure 3:
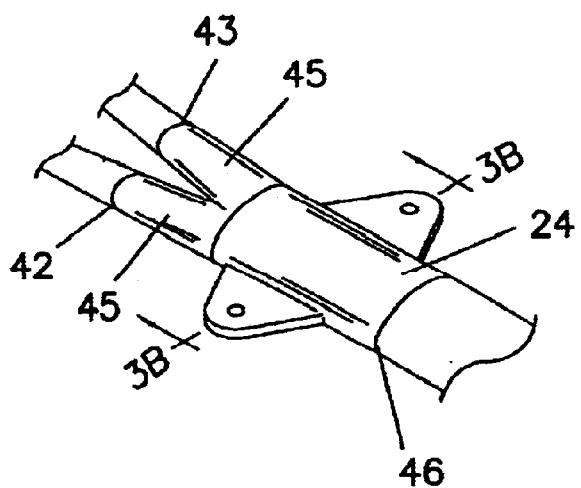
FIG. 3 is an enlarged perspective view of the hub in the catheter assembly of FIG. 1.
Figure 3B:
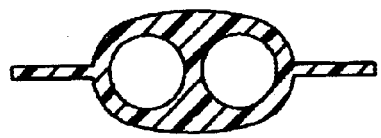
FIG. 3B is a cross sectional view of the hub of the multilumen catheter assembly of FIG. 3 taken along line 3B—3B.
Figure 3C:
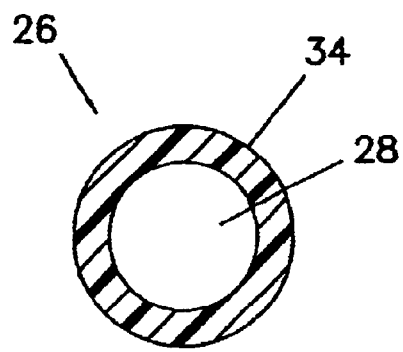

Preferably, the first and second distal end tubes 26, 30 and/or the passageways 28, 32 through the end tubes and the first and second lumens 22, 23 have a generally circular cross section as shown in FIGS. 1, 3A and 3C since it is most conducive to fluid flow properties. However other shapes such as D-shaped passageways and/or lumens, oval passageways and/or lumens, triangular, square, kidney-shaped or other configurations are also within the scope of the invention. Further, while the distal end tubes 26, 30 and the lumens 22, 23 are preferably identical in cross section, it is within the scope of the invention to vary the size, shape or configuration of the distal end tubes and lumens in cross section such that smaller tubes and/or lumens or varying types of lumens and distal end tubes may be used for other applications, such as addition of a third, smaller lumen and corresponding distal end tube for introduction of medication.

It is further within the scope of the invention that the distal end tubes have varying diameters or distal end shapes as are known in the art or to be developed. For example, the distal end tubes may have a larger diameter proximate to the unitary catheter which transitions abruptly or gradually to a smaller diameter proximate to the distal ends of the tubes. Alternatively, a more tapered, conical or angled distal end may be provided for varying applications. However, blunt ends, preferably formed of soft durometer material are preferred for the catheter and distal ends to provide comfort to the patient and avoid vessel wall trauma and stenosis.

The first and second distal end tubes 26, 30 have respective first and second distal ends 26a and 30a. Preferably, as shown in FIG. 1 the first distal end tube 26 has a length $l_1$ which is less than a length $l_2$ of the second distal end tube 30 when measured in a longitudinal direction along each of the distal end tubes 26, 30. As shown in FIG. 1, the catheter assembly 10 is curved to show that the catheter assembly including the distal end tubes 26, 30 are flexible, however, the catheter assembly 10 may be elongated to be fully extended in the longitudinal direction for the purposes of measuring $l_1$ and $l_2$ in a straight line along the distal end tubes. The distal end tubes preferably also have a plurality of holes 33 extending through the exterior surfaces 34, 40 of the distal end tubes 26, 30 to provide for additional or alternative flow paths for fluids flowing from between the area outside the tubes to the area inside the tubes and vice versa. Such holes 33 are preferably arranged in a circumferentially and helically around the tubes to provide optimal flow properties and avoid suctioning of the distal tubes against the area to be catheterized such as a vessel wall. Further, such holes minimize vibratory movement of the distal end tubes 26, 30 by equalizing the disturbances of intake and return flow through the apertures 33. Minimizing the vibratory movement helps prevent stenosis. The apertures 33 also provide alternative openings in the distal end tubes 26, 30 such that if flow becomes blocked at an opening 26b or 30b, dialysis can continue while a replacement catheter assembly is being provided.

FIG. 2 shows a cross-section of the unitary catheter 20, which shows that the unitary catheter 20 has first and second lumens 22, 23 which are co-extensive with the passageways 28, 32 in the first and second distal end tubes 26, 30, respectively. The unitary catheter 20 has a preferably smooth exterior surface 36, which is illustrated in the embodiment shown in FIGS. 1 and 2. Preferably the unitary catheter 20 has a transverse cross section which is generally oval in shape, although any transverse cross sectional shape may be used. Preferably, shapes which are curved and smooth are used, such as circular or kidney-shaped to provide for smooth insertion through a vessel wall or other body area. Further, by providing the unitary catheter 20 with a smooth, preferably curved outer surface as shown, when the catheter assembly is inserted into an area to be catheterized, such as a vessel, the area to be catheterized can seal around the unitary catheter 20 while the distal end tubes 26, 30 are preferably fully within the area to be catheterized and independently moveable.

A fabric tissue ingrowth cuff 44 or other similar subcutaneous securement device is preferably provided on the unitary catheter 20, which can be used to allow subcutaneous tissue or other body tissue depending upon the application of the catheter assembly to grow into the cuff 44 to thereby secure the catheter, preferably in chronic catheterizations. However, it will be understood based on this disclosure that other securement methods and devices known or to be developed may be used with the assembly and in methods according to the present invention.

With reference to FIG. 1, the catheter assembly preferably has extension tubes 38, 39 which are in fluid communication with the first and second lumens 22, 23 and the first and second passageways 28, 32 through the distal end tubes 26, 30, respectively of the unitary catheter 20 preferably through the hub 24. FIG. 3 shows the hub 24, which is formed around the exterior surfaces 38a, 39a of the distal ends 42, 43 respectively of the extension tubes 38, 39 and around a proximal end 46 of the unitary catheter 20. When forming the hub around the distal ends 42, 43 of the extension tubes 38, 39, it is preferred that the hub have projecting portions 45 configured to divert the extension tubes 38, 39 away from each other to facilitate keeping the lines from tangling or catching on each other. The extension tubes 38, 39 and the unitary catheter 20 are sealed within the hub 24 in a watertight seal.

The hub 24 is sealed, such as by bonding, adhering, heat molding or otherwise attaching the hub 24 to the distal ends 42, 43 of the extension tubes 38, 39 and proximal end 46 of the unitary catheter 20. In one embodiment of the invention, described in further detail below, the extension tubes 38, 39 are proximal portions of two separate catheters which are then coated with an outer layer, preferably by heat molding, to form the unitary catheter portion of the assembly. As such, the extension tubes 38, 39 are continuous with the unitary catheter 20 and the hub 24 can be simply molded or otherwise adhered around the end of the unitary catheter and around the proximally extending portions of the catheters within the outer layer.

The catheter assembly further preferably comprises connection devices for connecting the extension tubes 38, 39 to a hemodialysis unit. Any suitable connector may be used. Preferably, a detachable quick connect device is used such as that shown in FIG. 1. Such connector devices are known in the art and are commercially available on catheters available from Medical Components, Inc., Harleysville, Pa. As such they are described herein for convenience purposes, however, since other connectors may be used, while preferred, the connectors shown in FIG. 1 are optional.

The connectors in FIG. 1, described herein to have identical parts, have a first detachable fitting 48 which may be slidable along the extension tubes 38, 39, but quick connects, either by a snap-fit, screw threads or other suitable closure, preferably screw threads as shown in lines A in the partial cross sectional view of the connector in FIG. 1 to the end piece 50. Mating screw threads D may also be provided to the bottom of end piece 50 as shown in FIG. 1. The fitting and the end piece preferably include a tight fit, and may have a gasket or other seal device B as shown in FIG. 1 which is merely a silicone rubber cylindrically shaped gasket to ensure a tight fit. Other suitable sealing mechanisms to avoid detachment or slippage or leakage through the connectors and extension tubes are acceptable. The end pieces 50 are configured to have extending portions C shown in phantom in FIG. 1 which fit snugly into the proximal end openings of extension tubes thereby preferably a tight fit with the interior surfaces of the tubes 38, 39. When the end pieces 50 and fittings 48 are locked together, they hold the tubes securely.

The connector may have a further, replaceable and detachable connection section including detachable tubes 52 which are preferably made of a more resilient and easily replaceable material than extension tubes 38, 39. While this is not necessary, it enables the use of softer durometer materials to be used for the extension tubes, but avoids possible damage to them from clamps or quick changes to connect to hemodialysis equipment. Clamps 56 may also be provided to stop flow or seal off tubes when not in use. Standard luer locks 58 or similar connectors may be provided on the proximal ends of the tubes 52 to connect to dialysis equipment.

The distal end tubes 26 and 30 extend from the unitary catheter 20 and are formed by splitting an initially formed unitary catheter tube and by grinding and polishing to yield smooth, round tubes as described below. The hub 24 attaches the extension tubes 38, 39 to the unitary catheter 20.

The first distal end tube 26 and the second distal end tube 30, the unitary catheter tube 20, the extension tubes 38, 39 and the hub are all preferably made of biocompatible plastics or elastomers, most preferably biocompatible elastomers.

Suitable biocompatible plastics may be selected from materials such as, for example, polyurethane, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art. It should be understood that these possible biocompatible polymers are included above for exemplary purposes and should not be construed as limiting. If a biocompatible polymeric material is used to form the unitary catheter 20, distal end tubes 26, 30 and preferably the extension tubes 38, 39 it is most preferred that the polymeric material includes a polyurethane polymer or a polyolefin polymeric material having a preferably soft durometer, as specified below.

The extension tubes 38, 39 may be made separately from the unitary catheter and distal end tubes and formed of a material such as a polyurethane or a polyvinyl chloride polymer or elastomer. However, it is preferred that the extension tubes 38, 39 are formed of the same material as the unitary catheter and distal end tubes.

It is most preferred to use a biocompatible elastomer to form the unitary catheter, distal end tubes, hub and extension tubes. Suitable, preferred, biocompatible elastomers for use in forming the unitary catheter 20, distal end tubes 26, 30 and preferably the extension tubes 38, 39 include biocompatible elastomers such as medical grade silicone rubbers, polyvinyl chloride elastomers, polyolefin homopolymeric and copolymeric elastomers, urethane-based elastomers, and natural rubber or other synthetic rubbers. Preferably, the unitary catheter, distal end tubes and extension tubes are made of the elastomeric material such that they are flexible, durable, soft, and with respect to those portions inserted in the patient or tunneled, they are easily conformable to the shape of the area to be catheterized 12 and/or the subcutaneous area 16. Further, these materials help to minimize risk of harm to vessel walls.

If the catheter assembly 10 is used for hemodialysis applications, the unitary catheter 20, distal end tubes 26, 30 and preferably the extension tubes are most preferably formed of a soft silicone elastomer which has a hardness of from about 75-A to about 85-A on a Shore durometer scale. Suitable, preferred elastomers include silicone or polyurethane elastomers, and most preferably polyurethane elastomers, such as, for example, Pelletane® from Dow Corning, or as Tecothane®, Carbothane® or Tecoflex® available from Thermetics. The distal end tubes 26, 30 may also optionally be made such that they include 20% barium sulfate in the elastomer to provide radiopacity if desired. While it is preferred to have a Shore-A durometer hardness in the above Shore-A durometer range and a somewhat soft material, if a biocompatible elastomer is used, particularly for hemodialysis, it is also possible to make a device from an elastomer having a lower Shore-A durometer hardness outside this range, particularly one which is more rigid material if a particular application so requires, without departing from the spirit of the invention. It is also preferred that the hub is formed of an elastomeric material, and most preferably the same material as the remaining components of the assembly 10. However, the hub while preferably somewhat flexible, may also preferably be somewhat harder and more rigid, by about 5–10 points on the Shore-A durometer scale, than the unitary catheter, distal end tubes and extension tubes. It will be understood based on this disclosure that the softness or rigidity may be varied for different applications.

Most preferably, the unitary catheter 20 and distal end tubes 26, 30 are formed of Carbothane® of durometer of about 75-A, extension tubes 38, 39 of Carbothane® 75-A or 85-A and a Carbothane® hub of about 85-A durometer. Alternatively, a preferred combination may be formed of a Tecoflex® of durometer of about 80-A for the unitary catheter 20 and distal end tubes 26, 30, and a Pelletane® of durometer of about 80-A for the hub and/or extension tubes 38, 39. The additional components for attaching to dialysis or similar equipment including luers, connectors and the like are preferably formed of a polymeric and/or elastomeric material such as acetal, silicone 80-A or polyvinyl chloride. However, such connectors may be formed from any suitable material known or to be developed in the art for forming such connectors and/or adapters.

The invention further includes methods for making a multilumen catheter assembly such as the assembly of FIG. 1. The method will be illustrated with respect to FIG. 1 and FIGS. 7A–7D. The method includes forming a unitary catheter tube 60, which has a proximal portion 61, a distal portion 63 and a distal end portion 62 which terminates in a distal end 64. The unitary catheter tube 60, as shown in FIG.

7A, may be formed using any suitable heat molding process including injection molding, expansion/compression molding and extrusion. Preferably the unitary catheter tube 60 is formed by extrusion through a die to form internal lumens such as those shown for the device of FIG. 1 in FIG. 2. The lumens are preferably substantially the same and more preferably substantially identical in size and configuration. The tube 60 with internal longitudinally extending lumens may also be formed by injection molding the tube around metal rods which have the shape of the internal lumens. However, extrusion is most preferred.

Figure 7A:
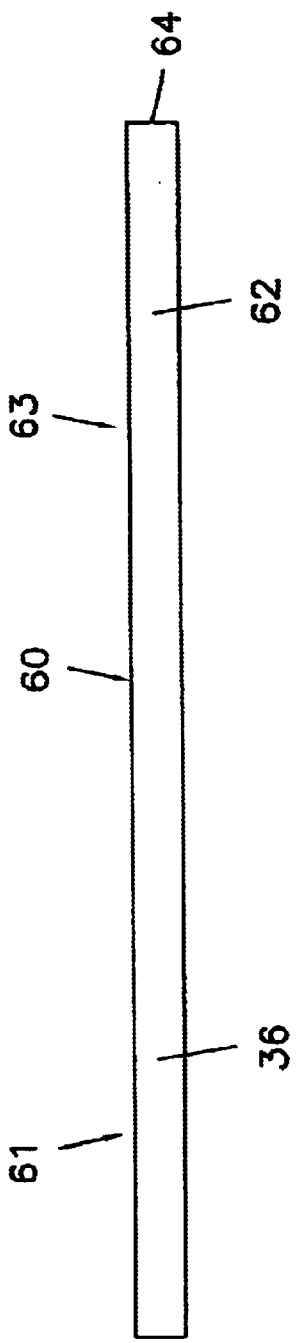
FIG. 7A is a partially broken away plan view of a unitary catheter tube for use in making a multilumen catheter according to one embodiment of the invention.
Figure 7B:
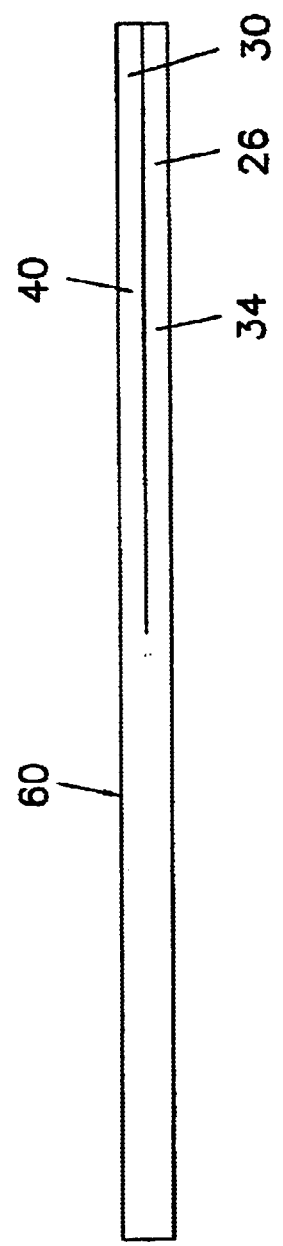
FIG. 7B is a partially broken away plan view of the unitary catheter tube of FIG. 7A which, has been split at the distal end to form distal end tubes.

As shown in FIG. 7B, the tube 60 is then split longitudinally along the distal portion 62 of the tube using a sharp edge such as a hot knife or razor blade (not shown) for a preferred distance, depending upon the particular size of the catheter. Preferably, the tube 60 is split a distance of from about 4 cm to about 6 cm, and most preferably about 9 cm extending to the distal end 64 of the unitary tube. The tube is preferably split as evenly as possible between the two lumens along the internal septum 66 (shown in FIG. 2). If more than one lumen were present, the unitary tube would be split equally along each internal septum with preferably a substantially equal amount of tubing material surrounding each of the split portions of the tube. Splitting the unitary catheter tube 60 forms a first distal end tube 26 and a second distal end tube 36. The first distal end tube is then cut to size such that it is shorter in length than the second distal end tube as shown in FIG. 1 for avoiding recirculation of fluids entering and leaving the tubes within the area to be catheterized 12.

Figure 7C:
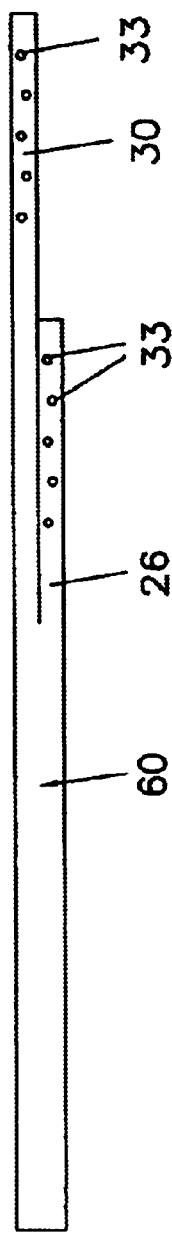
FIG. 7C is a partially broken away plan view of the unitary catheter tube of FIG. 7B after shortening the first distal end tube and forming a plurality of holes in the distal end tubes.

After the unitary catheter tube and distal tubes are formed, the exterior surface 36 of the unitary catheter tube and the exterior surfaces 34, 40 of the distal end tubes are then ground and polished by radio frequency (RF) tipping to provide a smooth surface. This process involves using RF energy to re-heat the outer surface until there is some melting and to polish the surface. Further, the distal end tubes 26, 30 preferably undergo this procedure on a mandrel such that they may be re-shaped to have a generally circular transverse cross section both in the interior passageways 28, 32 and on the exterior surfaces 34, 40 as shown in FIGS. 1, 2, 3A and 3B. Once the surfaces are shaped and smoothed, as shown in FIG. 7C, a plurality of holes 33 are then formed in the distal end tubes using techniques well known in the art such that the catheter tube 60 is now formed into a unitary catheter such as the unitary catheter 20 of FIG. 1.

As an alternative to splitting the unitary catheter, after forming the unitary catheter tube 60, distal end tubing of lengths $l_1, l_2$ (which may be previously extruded or heat molded) may then be fused onto the unitary catheter tube 60. The two distal end tubes are formed such that they have respectively longitudinal passageways 28, 32 extending therethrough, and may also be formed to include a plurality of holes 33 either prior to attaching to the distal end of the unitary catheter tube or such holes may be formed after attaching to the unitary catheter tube 60. The formed distal end tubes are then attached by a suitable heat molding or other form of attachment such as an adhesive, ultrasonic welding or other methods known in the art, to the distal end of the unitary catheter tube such that the first passageway in the first distal end tube is in communication with the first lumen of the unitary catheter tube and the second passageway in the second distal end tube is in communication with the second lumen in the unitary catheter tube. Preferably heat fusing is used to attach the distal end tubes, and the fusing may be carried out using heat applied to the unitary catheter tube and distal end tubing lengths in a female cavity mold to thereby create a smooth fused portion where the tube 60, and end tube lengths meet. The resulting structure would be of the same basic appearance of the device of FIG. 7B but formed differently. From there on, the structure may be formed as set forth with respect to unitary split catheter tube 60 in FIGS. 7A–7D, however, the resulting distal end tubes will preferably already have a smooth surface from the heat fusing and prior extrusion to shape such that further polishing and grinding as described herein would not be necessary. However, it will be understood that the present invention does not exclude such further shaping and/or polishing.

The extension tubes 38, 39 may be provided either by extruding or molding them initially when forming the unitary catheter tube 60 using techniques similar to those used to form the distal end tubes as described above. However, it is more preferred to attach the extension tubes to the proximal end 46 of the unitary catheter tube using the technique illustrated in FIG. 7D. Metal rods 68 are used which are bent to provide a desired angle of separation for the proximally extending projections 45 of the hub 24 once formed. The angle may be varied within the scope of the invention, preferably from about 25° to about 50°, and more preferably about 36°. The metal rods are inserted through the extension tubes 38, 39 and through the lumens within the unitary catheter tube 60 as formed in the manner described above. The extension tubes are spaced from the proximal end 46 of the unitary catheter tube 60 a distance slightly less than the size of the hub mold such that when the hub is molded around the extension tubes and unitary catheter tube, the hub will overlap the tubes for a watertight seal. The assembled rods and tubes are then placed in a mold and the hub 24 molded around the tubes as shown in phantom lines in FIG. 7D. After forming the extension tubes 38, 39 in connection by the hub to the unitary catheter tube 60, the metal rods are removed, and the connector assembly shown in FIG. 1 or another suitable connector are preferably then connected, either permanently or detachably as in FIG. 1 to form a complete and preferred multilumen catheter assembly such as the assembly 10 of the invention.

In one embodiment of the method of the invention, as shown in FIGS. 8A and 8B, a multilumen catheter may be made by arranging a first catheter 68 and a second catheter 70 in a substantially longitudinally parallel arrangement, preferably such that they are juxtaposed to each other, however, a gap may be present between the catheters 68, 70. Further, more than one catheter may be used and similarly arranged. Each of the catheters is preferably a single lumen catheter, however, multilumen catheters may also be used for some applications. The first and second catheters 68, 70 each have a respective distal end 72, 73, distal end portion 74, 75 and at least one lumen in each catheter which extend longitudinally therethrough which are preferably the same as the lumens 22, 23 formed in the unitary catheter tube 60 as shown in FIG. 2.

An outer layer 76 is formed around at least a portion 77 of the exterior surfaces 78, 80 of the first and second catheters 68, 70 which is proximal to the distal end portions 74, 75 of the catheters. The outer layer is preferably extruded around the two catheters. However, the arrangement of catheters and formation of the outer layer 76 may also be formed by extruding the two catheters simultaneously through dies while coextruding the outer layer 76 around the catheters 68, 70. However, the outer layer is coextruded only over a portion of the exterior surfaces of the catheters proximal to the distal end portions 74, 75. Once the outer layer is formed, sufficient heat molding capability may be applied to heat mold the first and second catheters together. The lumens are generally longitudinally parallel and the catheters are heat molded together, preferably in juxtaposed relation and fixed within the outer layer. The distal end portions of the catheters extend outwardly and distally from the portions of the exterior surfaces of the first and second catheters which are within the outer layer. Since the distal end portions are not connected, they are capable of independent movement. It is also within the scope of the invention to heat mold a fill material between the first and second catheters to ensure that a smooth, oval exterior surface is formed around the catheters once the outer layer is formed.

As with the method discussed above, extension tubes may be provided to the ends of the catheters if the outer layer is formed to extend to the proximal ends of the catheter tubes in the manner shown in FIG. 7D for the previous method. Alternatively, the outer layer is formed over only a portion of the catheters leaving separate proximal ends extending from the area of the outer layer in the proximal direction to form extension tubes. In such case, as shown in FIG. 8B, the proximal end portions which serve as extension tubes 38, 39 in the manner shown in FIG. 1 extend proximally from the proximal end 46 of the outer layer formed around the catheters which provides a unitary catheter 20 as in FIG. 1. A hub is then molded around the proximal end of the outer layer and around the sections 82, 83 of the proximally extending proximal end portions adjacent the outer layer. Preferably, to maintain the unitary catheter tube and extension tubes in place, the mold either has cavities to receive the tubes or, more preferably, metal rods such as metal rods 68 are inserted through the extension tubes and lumens within the formed unitary catheter portion to retain the shape of the lumens and hold the tubes in place. A plurality of holes 33 may also be provided to the distal end portions. After forming the hub, the catheter assembly preferably includes connectors and the like as described above.

The multilumen catheter assembly is preferably used in hemodialysis and may be inserted as described below. Referring to again to FIGS. 1–6, the first distal end tube 26 and the second distal end tube 30 are configured to be placed, or inserted into, the area to be catheterized 12 which is preferably an internal jugular vein 19 as shown in FIG. 6. The unitary catheter 20 is configured to extend into the area to be catheterized 12 through the entry point 112 into the vein 19. The unitary catheter 20 is also sufficiently long to be secured to the patient either by subcutaneously tunneling the unitary catheter 20 as shown in FIGS. 5 and 6 or by attaching to the outer skin of the patient as shown in FIG. 4.

In an embodiment of one method of inserting a catheter according to the present invention as shown in FIG. 4, described herein with respect to the embodiment of FIG. 1 for convenience purposes, the portion of the unitary catheter 20 which extends proximally out of the incision 110 formed in the patient for preferably acute catheterization may be secured to the skin 18 of the body 14 by a suitable fastening material 56, such as adhesive tape, or an exterior securement device (not shown) as shown in U.S. Pat. No. 5,776,111. This method of securing and positioning the catheter assembly 10 is typically used in emergency or acute catheterization.

In another embodiment of the present invention method as shown in FIGS. 5–6, a proximal end 81 of the unitary catheter 20 may be secured in a subcutaneous area such as a subcutaneous tunnel 16 formed through the body 14 and typically extending between a subcutaneous area near the insertion site 112 into the vessel and a caudal exit site as shown in FIG. 6. Methods of tunneling are known to those of ordinary skill in the art. Tunneling may be used in either chronic or acute procedures.

Referring to FIGS. 1 and 4–6, each of the catheters 26, 30 is configured to have a suitable length and width useful for insertion into the internal jugular vein 19 as described. The distal end tubes 26, 30 are of different lengths as described above and their ends 26a and 30a are proximally and longitudinally spaced from each other by a sufficient distance which is the difference between 11 and 12 which substantially prevents recirculation of the purified blood and blood to be purified. The distance is preferably from about 3 to about 4 centimeters, however, it should be understood by one of ordinary skill in the art, based on this disclosure, that the ends can be flush with each other and the distance between the ends 26a, 30a can be varied for different applications of the multilumen catheter assembly 10. Since blood flows toward the atrium, the blood flow in the internal jugular vein 19 is in a downward direction in FIGS. 4–6 as shown by the directional arrow in the vein 19. Thus, the distal end 30a of the second distal end tube 30 is "downstream" from the distal end 26b of the first distal end tube 26.

During use of the multilumen catheter assembly 10 for hemodialysis, blood is preferably drawn out of the internal jugular vein 19 (i.e., the arterial flow) through the distal end 26a of the first distal end tube 26 (upstream catheter) and returned (i.e., the venous flow) through the distal end 30a of the second distal end tube 30 (downstream catheter). This flow direction may be reversed depending upon the desired flow rate and concerns associated with approaching the atrium during hemodialysis for the internal jugular vein. It should be understood by one of ordinary skill in the art, based on this disclosure, that either direction of flow may be used provided that flow in both lumens for hemodialysis applications is in opposite directions. If flow is reversed to draw from near the atrium, higher flow rates for high flow rate dialysis devices of flow rates of about 450 cc/min may be achieved. The ability to use higher flow rates without collapse of the lumens, as in multiple lumen catheters, decreases the time necessary for a patient to undergo conventional dialysis treatments, a significant patient benefit.

Referring now to the acute catheterization procedure of FIG. 4 an incision 110 is initially made near an insertion site 112 which is to be aspirated with a syringe or other introducer apparatus near or proximate the area to be catheterized 12. If the multilumen catheter assembly 10 is used for hemodialysis and the area to be catheterized 12 is the internal jugular vein 19, the incision 110 is made in the clavicular triangle region, as shown for example, in FIG. 4. The exact location of the incision 110 can be varied by the physician. In accordance with the Seldinger technique, a narrow needle is inserted through the incision 110 and into the vein 19, and the vein aspirated. A guide wire is then passed through the needle, or other introducer, and the needle is removed. A dilator (not shown) and a tearable sheath are introduced over the guide wire and partially into the vein 19. While the sheath is not shown in FIG. 4, the sheath as used in the acute method is the same as the sheath 114 as shown in FIG. 6 with respect to the following description of the subcutaneous tunneling method. Once the sheath is in place, the guide wire is removed. The insertion site 112 is now ready to accept the catheter assembly 10.

The distal end tubes 26, 30 are inserted into, and through, the sheath in juxtaposed relationship. The distal end tubes 26, 30 are inserted until they are properly positioned within the area 12, as shown in FIG. 4 and the unitary catheter 20 extends through the vessel entry site 112. The sheath is then removed in the conventional manner, leaving the distal end tubes 26, 30 in the area 12. As shown in FIG. 4, the distal end tubes 26, 30 may freely move within the area 12.

Next, the incision 110 is closed and the proximal portion 81 of the unitary catheter 20 is secured to an external surface 18 of the body 14 by fastening material 84, such as adhesive tape. The incision 110 may also be closed after securement. While not necessary in acute catheterization, tunneling and subcutaneous securement can be effected by use of a trocar as discussed below with respect to chronic catheterization. The luer locks 58 are connected in fluid communication to respective fluid inlets and outlets of a hemodialysis unit, or other fluid transfer equipment (not shown) and dialysis may now begin.

The chronic catheterization procedure is now described with respect to FIGS. 5 and 6. Referring to FIG. 5, the unitary catheter 20 of the multilumen catheter assembly 10 may be located within a subcutaneous tunnel 86 in the subcutaneous area 16 of the body 14, using various tunneling techniques. In one technique, the distal end tubes 26, 30 are pulled through the tunnel 86 from the caudal end of the tunnel, while forming the tunnel using a trocar or other tunneling tool, leaving the proximal portion 81 of the unitary catheter 12 at least partially within the tunnel 86 and the distal end tubes 26, 30 extending outwardly from the opposite end of the tunnel 86 near the area to be catheterized 12. One technique for tunneling the distal end tubes 26, 30 through a subcutaneous area includes an elastomeric tube. A tunneling tool, e.g., a trocar, is generally already equipped with a 3 or 4 in (7.62 to 10.16 cm) elastomeric safety tube over its pointed, cutting end (not shown). If the trocar does not already have such a tube, any similar tube may be used in conjunction with the trocar. The safety tube may be slid down the trocar to capture the ends of the distal end tubes. Preferably, the gripping end of the trocar is first inserted into the lumen of the longer distal end tube. The tube may then be slid over the connected trocar and distal end tube to also capture the end of the shorter distal end tube. Using either technique, the connected trocar and distal end tubes 26, 30 are pulled through a subcutaneous tunnel made by the pointed end of the trocar. Once the catheters have been placed in the subcutaneous area, and prior to inserting the distal end tubes 26, 30 into the area to be catheterized 19, the tubes 26, 30 and portion of the unitary catheter 20 extending from the patient appear as shown in FIG. 5.

Referring now to FIGS. 5 and 6, an incision 110 is made at the insertion site 112, either before or after tunneling, and the distal end tubes 26, 30 are inserted into, and through, the sheath 114 in a juxtaposed manner, in the same manner as described above with respect to FIG. 4. The remaining catheter insertion and incision closure steps are the same as those described above with respect to FIG. 4. After the multilumen catheter assembly 10 is inserted as shown in FIG. 6, the incision is closed and the unitary catheter 20 of the assembly 10 is substantially below the skin of the patient. Lastly, the open ends of the luer locks 58, extending caudally from the tunnel, are attached in fluid communication with respective fluid inlets and outlets of a hemodialysis unit, or other fluid transfer equipment (not shown), and dialysis can begin.

To further ensure that the proximal portion 81 of the unitary catheter remains secured in the subcutaneous area 16 of the body 14, one or more anchoring members, such as a tissue ingrowth cuff 44 may be positioned around (i.e., circumferentially disposed on) the proximal portion 81 of the unitary catheter 20, such that the anchoring members will be situated in the subcutaneous area 16 after tunneling, as is well-known in the prior art.

The present invention provides the advantages of a Tesio or Schon multiple catheter assembly, in that it has two freely movable distal tips, while also providing the advantages of a single insertion method, and the ability to easily manipulate the proximal portion of the unitary catheter 20 and tunnel with only one tunneling procedure. The unitary catheter 20 has a smooth, generally convex exterior surface, which passes through the insertion site 112. With reference to FIG. 6, vessel wall 19a can readily seal around the smooth curved surface of the unitary catheter 20. If the distal end tubes 26 and 30 were located at the insertion site 112, the vessel wall 19a would not be able to ensure as tight a seal, because there would still be a potential risk of leakage between the tubes which would form a figure-8 configuration.

By having the unitary catheter 20, which has the smooth, generally curved surface, the vessel wall 19a can seal quite well around the surface particularly well with a ligature. Since there is a good seal at the insertion site 112, the risk of blood loss around the unitary catheter 20 is minimized.

The smooth, round distal end tubes 26 and 30 do not have any protuberances on their surfaces that would promote clotting. A rough external surface provides protuberances, which can be points where clotting can begin. The distal end tubes 26 and 30 have smooth, round exterior surfaces that float freely within the vessel 19, which do not provide a source of clot formation. The free-floating distal end tubes 26 and 30 provide the many advantages of an individual catheter tube, such as provided by a Tesio catheter, including no tendency to suction against an inside surface of the vessel wall 19a, which minimizes the tendency of stenosis. The multilumen catheter assembly 10 further has little tendency to kink, since the unitary catheter 20 has a good deal of support due to the thickness of its walls and cross-section and due to the smoothness of the separate catheter tubes.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A multilumen catheter assembly having a distal portion, wherein the catheter assembly comprises:

a unitary catheter body having a plurality of lumens disposed therein, wherein the entire body has a generally oval cross section, wherein the unitary catheter body includes a longitudinal plane generally bisecting the unitary catheter body;

wherein the plurality of lumens comprises:

a first lumen disposed within the unitary catheter body on a first side of the longitudinal plane, wherein the first lumen is generally circular in cross section and has a first length; and a second lumen disposed within the unitary catheter body on a second side of the longitudinal plane, opposing the first side of the longitudinal plane, wherein the second lumen is generally circular in cross section and has a second length, different from the first length;

wherein the distal portion of the catheter assembly is split along the longitudinal plane such that each of the first and second lumens is capable of free movement independent of the other of the first and second lumens, wherein the catheter assembly further comprises a first extension tube in fluid communication with the first lumen and a second extension tube in fluid communication with the second lumen.

2. The multilumen catheter assembly according to claim 1, further comprising a first extension tube in fluid communication with a first lumen and a second extension tube in fluid communication with the second lumen.

3. The multilumen catheter assembly according to claim 2, wherein the hub is configured to divert the distal ends of the extension tubes away from each other.

4. The multilumen catheter assembly according to claim 1, further comprising a connector and a clamp releasably attached to each extension tube.

5. The multilumen catheter assembly according to claim 1, further comprising a plurality of holes formed through each of the first and second distal end tubes to provide fluid flow from outside the first and second distal end tubes into the passageways in the first and second distal end tubes.

6. The multilumen catheter assembly according to claim 1, further comprising a first distal end opening in the first distal end tube and a second distal end opening in the second distal end tube.

7. A multilumen catheter assembly having a distal portion, wherein the catheter assembly comprises:
   a unitary catheter body having a plurality of lumens disposed therein, wherein the entire body has a generally circular cross section, wherein the unitary catheter body includes a longitudinal plane generally bisecting the unitary catheter body;
   wherein the plurality of lumens comprises:
      a first lumen disposed within the unitary catheter body on a first side of the longitudinal plane, wherein the first lumen is generally circular in cross section and has a first length; and
      a second lumen disposed within the unitary catheter body on a second side of the longitudinal plane, opposing the first side of the longitudinal plane, wherein the second lumen is generally circular in cross section and has a second length, different from the first length;
   wherein the distal portion of the catheter assembly is split along the longitudinal plane such that each of the first and second lumens is capable of free movement independent of the other of the first and second lumens,
   wherein the catheter assembly further comprises a first extension tube in fluid communication with the first lumen and a second extension tube in fluid communication with the second lumen.

8. The multilumen catheter assembly according to claim 7, further comprising a connector and a clamp releasably attached to each extension tube.

9. The multilumen catheter assembly according to claim 7, further comprising a plurality of holes formed through each of the first and second distal end tubes to provide fluid flow from outside the first and second distal end tubes into the passageways in the first and second distal end tubes.

10. The multilumen catheter assembly according to claim 7, further comprising a first distal end opening in the first distal end tube and a second distal end opening in the second distal end tube.

* * * * *